United States Patent [19]
Leong

[11] Patent Number: 6,058,878
[45] Date of Patent: May 9, 2000

[54] PROTOZOAN FREE COLONIES OF LEPIDOPTERA

[75] Inventor: Kingston L. H. Leong, San Luis Obispo, Calif.

[73] Assignee: California Polytechnic State University Foundation, San Luis Obispo, Calif.

[21] Appl. No.: 09/098,895

[22] Filed: Jun. 17, 1998

[51] Int. Cl.[7] .................................................. A01K 29/00
[52] U.S. Cl. .................................................. 119/6.5; 800/8
[58] Field of Search .................................. 800/13, 22, 8; 119/6.5

[56] References Cited

PUBLICATIONS

Leong et al. Ecological Entomology. 17:338–342, 1992.
Altizer et al. J. Invert. Path. 74:76–88, 1999.
Leong et al. J. Invertebrate Pathology 69:79–83, Jan. 1997.
Leong et al. Pan–Pacific Entomologist 73(1):49–51, 1997.

Leong et al., "The occurrence and effect of a protozoan parasite, *Ophryocystis elektroscirrha* (Neogregarinida: Ophryocystidae) on overwintering monarch butterflies, *Danaus Plexippus* (Lepidoptera: Danaidae) from two California winter sites," *Ecological Etomology* 17, 338–342 (1992).

Leong et al., "Instar Susceptibility of the Monarch Butterfly (*Danaus plexippus*) to the Neogregarine Parasite, *Ophryocystis elektroscirrha*, " Journal of Invertebrate Pathology, 69, 79–83 (1997).

Leong et al., "Occurrence of a Neogregarine Protozoan, *Ophryocystis Elektroscirrha*, McLaughlin and Myers, In Populations of Monarch and Queen Butterflies", *Pan–Pacific Entomologist* 73(1), 49–51 (1997).

*Primary Examiner*—Scott D. Priebe
*Assistant Examiner*—Sumesh Kaushal
*Attorney, Agent, or Firm*—Gerstman, Ellis & McMillin, Ltd.

[57] ABSTRACT

A method for the establishment and maintenance of colonies of Lepidoptera which are free of contamination with protozoa is provided. The colonies consists of individuals capable of breeding and producing viable, noncontaminated butterflies.

2 Claims, No Drawings

PROTOZOAN FREE COLONIES OF LEPIDOPTERA

FIELD OF THE INVENTION

The present invention relates to the establishment and maintenance of protozoan free colonies of Lepidoptera.

BACKGROUND OF THE INVENTION

The order Lepidoptera includes butterflies and moths. The members of the order Lepidoptera and, especially, butterflies are considered by most persons to be among the most interesting and beautiful animals. Considerable interest has developed in raising butterflies for commercial purposes. This is especially true for members of the family Danaidae including monarch butterflies, *Danaus plexippus* (L.), and queen butterflies, *Danaus gilippus berenice* Cramer.

The monarch butterfly is known for its beauty and for its long distance migrations and mass winter aggregations in sites located in California and in Mexico. Recently, interest in this species has extended to raising this butterfly for sale to elementary schools and for release at weddings and other ceremonies and celebrations.

Breeders of monarch butterflies have encountered severe problems with a naturally occurring neogregarine parasite, *Ophryocystis elektroscirrha* McLaughlin and Myers. After 3 to 4 generations of rearing the butterflies under laboratory conditions, this parasite builds to an inoculum level that causes large numbers of deformed, weak butterflies, leading to the demise of the colony. The re-establishment of a colony of monarch butterflies from wild populations would eventually lead to another build up of the disease and to the destruction of the colony.

The temporary suppression of the disease in laboratory reared monarch butterflies has been previously accomplished by treating eggs with 2% bleach for 30 minutes. Although this treatment resulted in an apparently "clean" colony of butterflies, the colony eventually had to be destroyed because it was contaminated with neogregarine spores which had developed resistance to bleach. Eighty percent of eggs treated with 2% bleach for 30 minutes resulted in adult butterflies with high numbers of spores and some were weak and deformed.

This neogregarine protozoa has also been found to infect queen butterflies. Many populations of the queen butterfly are found in habitats shared with monarch butterflies where they feed on similar nectar sources and the larvae of the two species have been reported on the same milkweed host. It is quite likely therefore that the neogregarine protozoa is transmitted between the two species.

I have developed a method of establishing and maintaining colonies of butterflies which are free of contamination with protozoa through examination of pupa exuviae or the bodies of adults and by selection of non-infected individuals as breeders.

SUMMARY OF THE INVENTION

In accordance with the present invention, a method for obtaining colonies of Lepidoptera which are free of protozoan contamination is provided. The method involves performing an analysis for the presence of protozoan spores on the pupa exuviae or the bodies of adults. Adults which show no evidence of protozoan contamination on their pupa exuviae or bodies are selected and bred. The progeny of these monarch butterflies are isolated and raised. The steps of analyzing for spores, selecting and breeding noncontaminated adults, and isolating and raising their progeny are repeated until a generation is obtained in which none of the pupa exuviae and bodies of adults shows any evidence of protozoan contamination.

The colonies of the present invention have no individuals which are contaminated with protozoans and comprise individuals which can breed and produce normal, healthy, viable progeny which are noncontaminated. These colonies are capable of being maintained indefinitely.

DETAILED DESCRIPTION OF THE ILLUSTRATIVE EMBODIMENT

The benefit and utility of the present invention has been proven through experimental studies performed to produce neogregarine free colonies of monarch butterflies. It should be understood however that the work described below is only an illustrative embodiment and that the invention is broader.

For example, various methods are available for performing the analysis for the presence of protozoan spores. In addition to the visual inspection of chrysalides' exuviae, the spores could be detected using chemical assays, immunoassays, fluorescence, enzymes, or other detection, visualization or marking techniques. In addition, the presence of the spores could be determined after being removed from the pupa exuviae or bodies of the adults by washing or using tape.

A group of monarch butterflies (10 females and 10 males) was field collected from their overwintering site at Pismo North Beach, San Luis Obispo County, Calif., and kept in cages under greenhouse conditions (27.5° C.±3.7 and RH 66.0%±8.1) with natural light illumination. The adults were fed a 10% honey-water solution contained in a modified plastic (tissue culture) container. The top of the plastic container was perforated with holes to allow the butterflies access to the honey-water solution. The food mixture was replenished every two days.

The mating cages, 11.3 cm×15 cm, were constructed of a steel frame covered with aluminum screens so that they could be sterilized within the autoclave. The cages were large enough to permit normal mating and feeding activities of the adult butterflies.

Upon mating, the pairs were placed in separate oviposition cages containing a milkweed bouquet and a container of honey-water. The oviposition cage was a modified 5 gallon ice cream container, with a door flap cut into the side and a netted cloth material covering the opening. The cloth material was secured to the mouth of the ice cream container by a sleeve made up of the hollowed-out cover lid. When the pair uncoupled, the male was removed and sacrificed. The milkweed bouquet and the solution of honey-water were replenished every two days until the female expired. The oviposition container was sterilized by autoclaving before using the container for another mated pair.

The oviposition bouquet consisted of Blood flower milkweed, *Asclepias curassavica* (L.), or Crown flower milkweed, *Calotropis gigantea* (L.), cuttings 15 cm to 20 cm in length. The bottom ends of the cuttings were inserted through the middle openings of two drinking and coffee cup lids, secured (top surfaces) together with staples. The bottom lid was secured to the mouth of a water filled styrofoam cup. The milkweed bouquet was presented to the female every two days in the oviposition cages.

The milkweed bouquet with eggs of each female was removed and enclosed in a inverted drinking cup that was secured to its lid at the base of the bouquet. The drinking cup was modified by cutting out the bottom and covering this opening with Kimwipe tissue. The tissue was secured to the cup with tape.

The larvae were reared under laboratory conditions (20.6° C.±3.2 and RH 56.5 %±8.9) on these bouquets and were transferred to individual containers (plastic cups and lids), one per container, when they reached the 4th instar. The container had 5 holes on the top (cup's bottom) for aeration. The larvae were fed daily with Crown flower milkweed leaves, Blood flower milkweed leaves or a semi-artificial diet containing milkweed leaves until pupation. Upon emergence, the chrysalides of the adults were examined for protozoan spores. The plastic cups were used only once to avoid contamination.

The Blood flower milkweed and the Crown flower milkweed were grown in an enclosed greenhouse to avoid contamination from "wild" monarch butterflies with neogregarine spores and to provide a food supply for year-round reading of butterflies. The semi-artificial diet was sterilized in an autoclave to avoid contamination.

The selection of breeders for each generation was made among cohorts with the least number of infected individuals based upon the visual absence of neogregarine spores on their chrysalides' exuviae. The abdominal section between the left and right rows of spiracles of the chrysalis exuviae was carefully cut with a flame sterilized scissors and placed on a glass slide. After adding a drop of water and a cover slip, the slide preparation was examined for protozoan spores under a compound light microscope, using 100 X magnification.

Random mixed matings of 10 males and 10 females, collected from the wild, yielded 96 adult butterflies (F1 generation). Forty-five (46.9%) of these had clean chrysalides.

Four random mated pairs were selected from the "clean" butterflies and used as breeders. The first sample batch of eggs of all F1 females produced infected individuals and 3 of 4 females produced infected offspring in all three egg samples. Female 1 produced 6 adults with clean chrysalides' exuviae in the second egg sample.

Seven pairs, with clean pupal exuviae, were randomly selected among the F2 as breeders. The three egg samples among the F2 females at 1–2, 6–7 and 12–13 day intervals produced 11.1% to 0% infected offspring. Females 7 and 10 produced clean offspring in all samples. Due to the number and duration of clean offspring produced, only butterflies from females 7 and 10 were used as breeders for the F3 generation.

Two females of the F3 generation produced offspring with visually clean chrysalides' exuviae. Butterflies from 12 were used for the F4 generation due to the number and duration of clean offspring produced. Five random mated pairs among the "clean" butterflies were selected and used as breeders for the F4 generation. These females produced a total of 184 butterflies, all free of protozoan spores.

Table 1 provides data from this experimental study. As shown, the incidence of infection showed a sharp decline from 53.1% to 0% after three generations of selection. The fourth generation remains disease free.

TABLE 1

| Generation | Female # | Total # Progeny | # Clean Progeny (# Infected Progeny) On Each Sampling Date | | | | % Infection |
|---|---|---|---|---|---|---|---|
| Wild (Parent) | — | 96 | 45(51) | | | | 53.1 |
| F1 | 1 | 34 | 28(4) | 6(0) | — | | 13.3 |
| | 2 | 38 | 12(1) | 19(5) | 7(1) | | 18.4 |
| | 3 | 29 | 4(3) | 15(5) | 10(2) | | 34.5 |
| | 4 | <u>92</u> | 49(7) | 21(3) | 22(5) | | <u>16.3</u> |
| | | 193 | | | | | 20.6 |
| F2 | 5 | 57 | 39(2) | 10(0) | 8(0) | | 3.5 |
| | 6 | 48 | 26(1) | 20(0) | 2(0) | | 2.1 |
| | 7 | 28 | 20(0) | 8(0) | — | | 0 |
| | 8 | 8 | — | — | — | | 0 |
| | 9 | 24 | 9(1) | 7(1) | 8(0) | | 8.3 |
| | 10 | 27 | 20(0) | 4(0) | 3(0) | | 0 |
| | 11 | <u>45</u> | 23(2) | 20(3) | 2(0) | | <u>11.1</u> |
| | | 237 | | | | | 3.6 |
| F3 | 12 | 55 | 27(0) | 9(0) | 18(0) | 11(0) | 0 |
| | 13 | <u>44</u> | 12(0) | 2(0) | — | — | <u>0</u> |
| | | 69 | | | | | 0 |
| F4 | 14 | 51 | 24(0) | 23(0) | 4(0) | | 0 |
| | 15 | 3 | — | — | 3(0) | | 0 |
| | 16 | 34 | 21(0) | 10(0) | 3(0) | | 0 |
| | 17 | 35 | 25(0) | 2(0) | 8(0) | | 0 |
| | 18 | 41 | 24(0) | 12(0) | 5(0) | | 0 |
| | 19 | <u>20</u> | — | 10(0) | 10(0) | | <u>0</u> |
| | | 184 | | | | | 0 |

The absence of neogregarine spores on a chrysalis' exuviae does not insure a "clean" butterfly, since the sensitivity of this visual examination can not differentiate between individuals with low, undetectable spore loads from those butterflies that are free of infection. The only means of evaluating the presence or absence of a spore load of a mated female by isolating the female and recording the incidence of infected progeny she will produce during her life. Depending upon the level of the spore load, a female may produce infected progenies throughout her life or only during her early egg laying days. Inoculum on a female with a light spore load would be depleted and clean eggs and offspring would eventually be produced.

Females that produce no infected progenies during their lifetime have better probability of being free of infection. Should the offspring of such a female or a combination of cohorts be allowed to mate and clean butterflies are produced, one can assume that a clean colony has been achieved. These conditions have been actualized.

Although an illustrative embodiment of the invention has been described, it is to be understood that various modifications and substitutions may be made by those skilled in the art without departing from the novel spirit and scope of the present invention.

What is claimed is:

1. A method for obtaining a neogregarine free colony of monarch butterflies comprising:
    (a) visually examining the chrysalides' exuviae of monarch butterflies for neogregarine spores;
    (b) selecting and breeding monarch butterflies with chrysalides' exuviae with no visible neogregarine spores;
    (c) isolating and raising the progeny of the selected monarch butterflies; and
    repeating steps (a), (b) and (c) until visual inspection of the chrysalides' exuviae fails to detect the presence of neogregarine spores for two generations of monarch butterflies.

2. A method of obtaining a neogregarine free colony of danaid butterflies comprising:

(a) performing an analysis for the presence of neogregarine spores on pupa exuviae or bodies of adults;

(b) selecting and breeding adults which show no evidence of neogregarine contamination on their pupa exuviae or bodies;

(c) isolating and raising the progeny of said selected adults; and repeating steps (a), (b) and (c) until a generation is obtained in which none of the pupa exuviae and bodies of adults shows any evidence of neogregarine contamination.

* * * * *